US00PP21706P2

(12) United States Plant Patent
Saul

(10) Patent No.: US PP21,706 P2
(45) Date of Patent: Feb. 8, 2011

(54) ***KNIPHOFIA* PLANT NAMED 'ECHO MANGO'**

(50) Latin Name: *Kniphofia uvaria*
Varietal Denomination: Echo Mango

(75) Inventor: Richard G. Saul, Cleveland, GA (US)

(73) Assignee: Itsaul Plants, LLC, Alpharetta, GA (US)

( * ) Notice: Subject to any disclaimer, the term of this patent is extended or adjusted under 35 U.S.C. 154(b) by 0 days.

(21) Appl. No.: 12/653,154

(22) Filed: Dec. 9, 2009

(51) Int. Cl.
*A01H 5/00* (2006.01)

(52) U.S. Cl. ..... Plt./443
(58) Field of Classification Search ..... Plt./443

See application file for complete search history.

*Primary Examiner*—Annette H Para
(74) *Attorney, Agent, or Firm*—Penny J. Aguirre

(57) ABSTRACT

A new cultivar of *Kniphofia,* 'Echo Mango', characterized by its inflorescences that are apricot in color, its early blooming habit with the first blooms appearing at the end of April to the first part of May in Georgia, its repeat bloom throughout the summer with up to 12 blooms per stem per season, its semi-evergreen foliage that remains clean, and its upright stems that reach 40 inches in height and do not lodge.

2 Drawing Sheets

Botanical classification: *Kniphofia uvaria.*
Varietal denomination: 'Echo Mango'.

BACKGROUND OF THE INVENTION

The present invention relates to a new and distinct cultivar of *Kniphophia uvaria* and will be referred to hereafter by its cultivar name, 'Echo Mango'. 'Echo Mango' is a new cultivar of red hot poker or torch lily, a perennial grown for landscape use.

The new cultivar was derived from a controlled breeding program conducted by the Inventor at his nursery in Dahlonega, Ga. The overall purpose of the breeding program is to make selections of *Kniphofia* with unique flower colors combined with a reblooming habit. 'Echo Mango' was selected in the Inventor's trial bed in June 2007 as a single unique plant from amongst the seedlings derived from a cross made in April 2006 between 'Apricot Surprise' (not patented) as the female parent and 'Candle Light' (U.S. Pat. No. 12,343) as the male parent.

Asexual reproduction of the new cultivar was first accomplished by division by the Inventor in Dahlonega, Ga. in June of 2007. The characteristics of this cultivar have been determined both by division and in vitro propagation to be stable and to reproduce true to type in successive generations.

SUMMARY OF THE INVENTION

The following traits have been repeatedly observed and represent the characteristics of the new cultivar of *Kniphofia.* These attributes in combination distinguish 'Echo Mango' from all other selections of *Kniphofia* known to the Inventor.

1. 'Echo Mango' exhibits an early blooming habit with the first blooms appearing at the end of April to the first part of May in Georgia.
2. 'Echo Mango' exhibits a reblooming habit with repeat bloom throughout the summer with up to 12 blooms per clump per season.
3. 'Echo Mango' exhibits semi-evergreen foliage that remains cleaner than is typical of the species.

4. 'Echo Mango' exhibits a clump-forming habit with upright stems that do not lodge.
5. 'Echo Mango' reaches a height of 100 cm (40 inches).
6. 'Echo Mango' exhibits inflorescences that are apricot in color.

'Echo Mango' can be distinguished from its parent plants. The female parent, 'Apricot Surprise', differs from 'Echo Mango' in being shorter in height, in having a habit that tends to flop, and in having flowers that are yellow in color. The male parent, 'Candle Light', differs from 'Echo Mango' in lacking a reblooming habit and typically averages 3 blooms per season. 'Echo Mango' can be distinguished from the species, *Kniphofia uvaria,* in having a reblooming habit and stems that remain upright. 'Echo Mango' can also be compared to the cultivar 'First Surprise' (U.S. Plant Pat. No. 16,036). 'First Surprise' is similar to 'Echo Mango' in its early blooming habit but differs from 'Echo Mango' in being shorter in height, in lacking a reblooming habit, and in having inflorescences that are bright orange in color.

BRIEF DESCRIPTION OF THE DRAWING

The accompanying colored photographs illustrate the overall appearance and distinct characteristics of the new *Kniphofia.* The photographs were taken of a 2 year-old plant as grown in a garden in Atlanta, Ga.

The photograph in FIG. 1 illustrates the overall habit and appearance of 'Echo Mango' in bloom.

Figure 1:
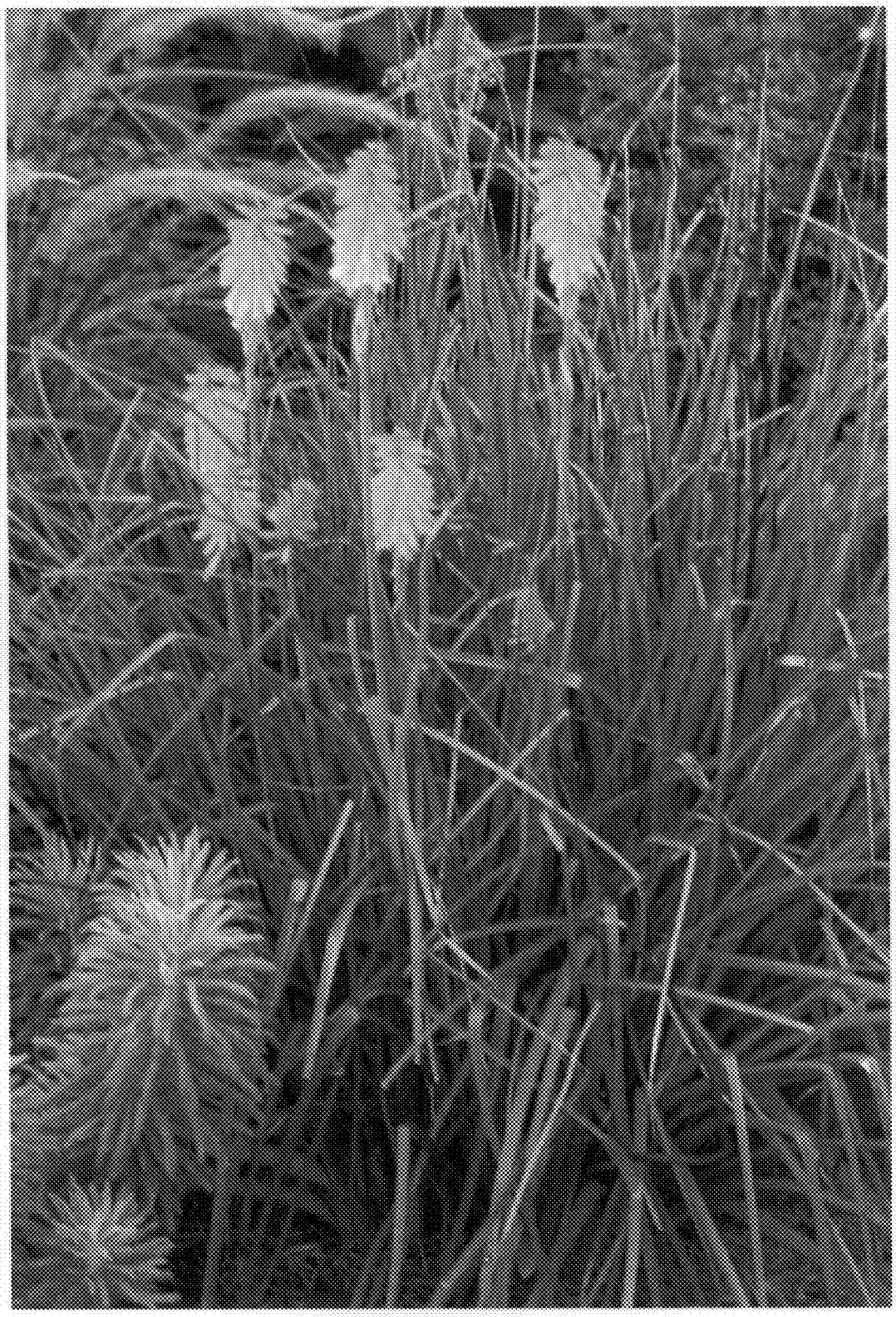
Figure 2:
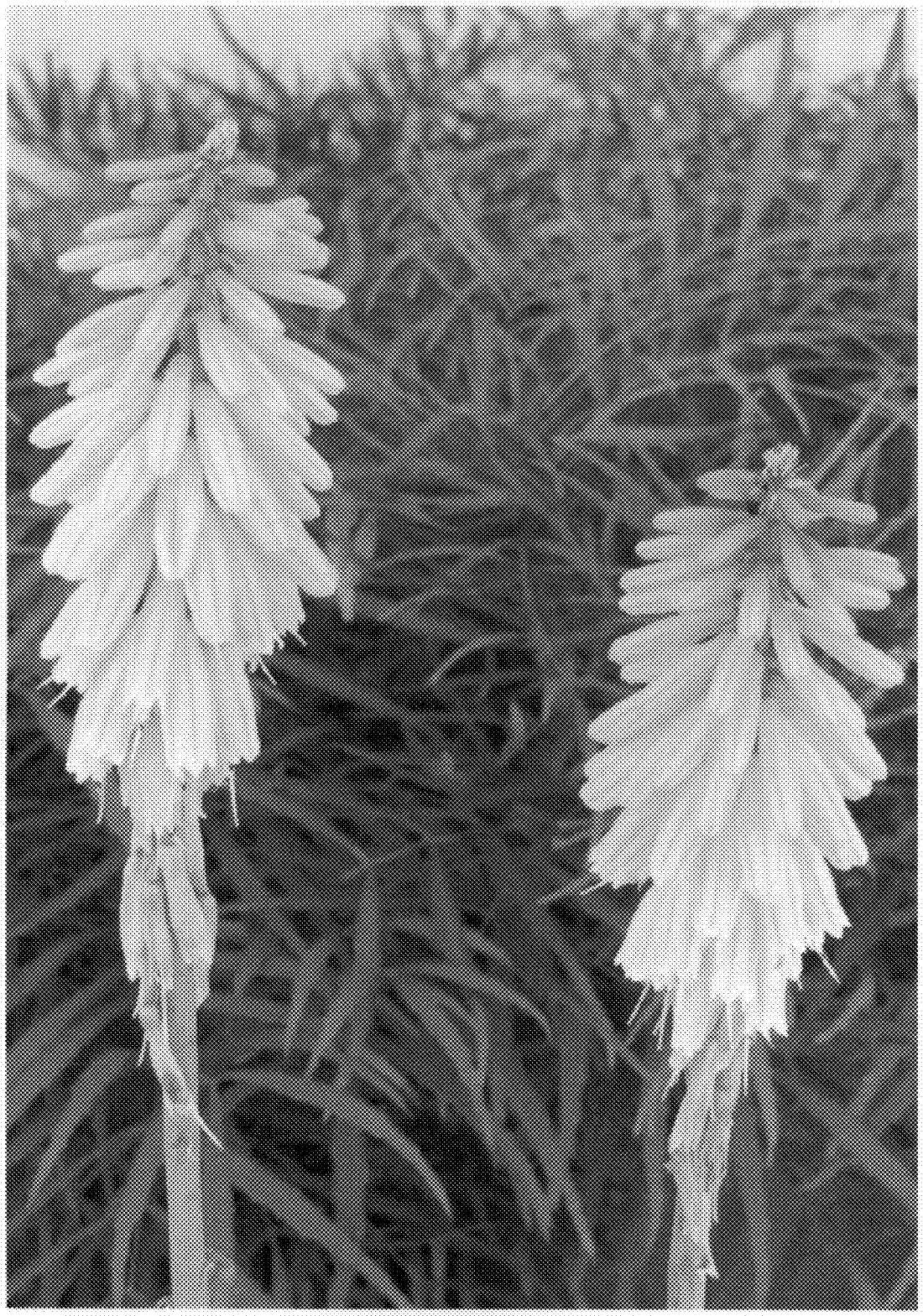

The photograph in FIG. 2 provides a close-up view of the inflorescences of 'Echo Mango'. The colors in the photograph may differ slightly from the color values cited in the detailed botanical description, which accurately describe the colors of the new *Kniphofia.*

DETAILED BOTANICAL DESCRIPTION

The general observations describe plants of 'Echo Mango' that were observed for 2 years in a trail garden in Dahlonega, Ga., while the detailed botanical data describe one year-old plants as grown in one-gallon containers in Alpharetta, Ga. The phenotype of the new cultivar may vary with variations in environmental, climatic, and cultural conditions, as it has not been tested under all possible environmental conditions. The color determinations are in accordance with The 2007 R.H.S. Colour Chart of the Royal Horticultural Society, London, England, except where general color terms of ordinary dictionary significance are used.

General description:

*Blooming habit.*—Blooms in April and then repeated throughout the summer.

*Plant type.*—Semi-evergreen perennial.

*Plant habit.*—Upright with foliage slightly cascading but without lodging, clump-forming basal grass-like leaves with upright flowers stems emerging from center of each division.

*Height and spread.*—About 100 cm (40 inches) in height in bloom and 61 cm (24 inches) in spread.

*Hardiness.*—U.S.D.A. Zones 6 to 9.

*Diseases and pests.*—No unique aspects concerning susceptibility or resistance to diseases or pests has been observed.

*Environmental stresses.*—Semi-evergreen foliage remains clean (cleaner than is typical of the species).

*Root description.*—Fleshy and thick.

Growth and propagation:

*Propagation.*—Tissue culture or division.

*Time required for root development.*—A 2-inch plug can be finished in about 5 to 6 weeks at 25° C. in summer (6 to 7 weeks in winter) from a division, and in about 6 weeks at 27° C. in summer (8 weeks in winter) when produced by tissue culture.

*Growth rate.*—Vigorous.

Foliage description:

*Leaf shape.*—Linear.

*Leaf division.*—Simple.

*Leaf base.*—Truncate and sheathed to base of shoot.

*Leaf apex.*—Narrowly acuminate.

*Leaf aspect.*—Sulcate, leaves initially emerge upright, then upright to slightly cascading.

*Leaf venation.*—Parallel, the midrib is raised on the lower surface, not prominent or conspicuous, color matches leaf color.

*Leaf margins.*—Entire, scabrous.

*Leaf attachment and arrangement.*—Sessile, arise in rosette-like.

*Leaf size.*—Average of 1 cm in width (at midpoint) and up to about 50 cm in length when mature.

*Leaf number.*—Average of 16 per rootstock (shoot).

*Leaf surface.*—Puberulent on upper and lower surface.

*Leaf color.*—Newly emerging leaves upper and lower surfaces: 144A becoming 145A new base, mature leaves upper and lower surface; 137A becoming a blend of 144A and 145A near base.

Flower description:

*Inflorescence type.*—Dense racemes of single flowers held on erect and strong scapes.

*Inflorescence size.*—Reaches up to 9 cm in height and about 6 cm in width.

*Flower fragrance.*—None.

*Flower quantity.*—An average of 55 flowers per raceme, up to 12 racemes per clump in a season.

*Flower lastingness.*—Flowers open from base towards the apex, average of 5 days per flower, not persistent.

*Flower buds.*—Oblong-obovate in shape, average of 2.5 cm in diameter and 5 mm in length, emerge 23A in color and mature to 15A with fine stripes and suffusion of 23B.

*Flower aspect.*—Held horizontally then slightly downward at about a 45° angle as they mature.

*Flower shape.*—Narrowly campanulate-tubular.

*Flower size.*—About 2.3 cm in depth and 7 mm in diameter.

*Tepals.*—About 6, fused with triangular-shaped free apex about 3 mm in width and 2 mm in length, margin is entire, apex is broadly acute, upper and lower surface is glabrous and waxy, color when fully open outer and inner surface; a blend of 12C and 12D with thin lines of 17B, color fades to 20B.

*Peduncles* (*scapes*).—About 56 cm in length (from base of plant to top of raceme) and an average of 5.5 mm in width, held erect, strong, color is a blend of 144A and 144B, surface is glabrous and slightly glaucous.

*Pedicels.*—Average of 2 mm in length and 1 mm in width, 152C in color, surface is glabrous and waxy.

Reproductive organs:

*Gynoecium.*—1 Pistil, about 2.3 cm in length and <1 mm in width, stigma is crested, minute and 18A in color, style is about 2.2 cm in length and 18A in color, ovary is superior, oblong in shape, about 3 mm in length and 1.5 mm in width and 144D in color.

*Androcoecium.*—6 stamens, anthers are oblong in shape, dorsifixed, about 2 mm in length and 1.5 mm width and 7A in color maturing to 164B in color, filaments are about 1.8 cm in length and 151C in color, pollen was moderate in quantity and 8D in color.

*Fruit and seed.*—Capsules; produced more abundantly when grown outdoors, ovoid-globose in shape, 3-parted, about 9 mm in length and 8 mm in width, a blend of 144A and 147A in color maturing to a blend of N200A, N200B, and 199A on the outer surface and 199B on the inner surface, glaucous surface becoming woody when mature, seeds; 3 per capsule, 3.5 to 4 mm in length, 200A in color.

It is claimed:

1. A new and distinct cultivar of *Kniphofia* plant named 'Echo Mango' as herein illustrated and described.

* * * * *